United States Patent
Barron

(10) Patent No.: US 8,632,769 B2
(45) Date of Patent: *Jan. 21, 2014

(54) PROTEOLYTIC ENZYME FORMULATIONS

(76) Inventor: Jon Barron, Porter Ranch, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/600,068

(22) Filed: Aug. 30, 2012

(65) Prior Publication Data

US 2013/0004565 A1 Jan. 3, 2013

Related U.S. Application Data

(63) Continuation of application No. 12/376,964, filed as application No. PCT/US2007/075630 on Aug. 9, 2007, now Pat. No. 8,287,858.

(60) Provisional application No. 60/836,824, filed on Aug. 10, 2006.

(51) Int. Cl.
*A61K 38/43* (2006.01)
*A61K 38/54* (2006.01)

(52) U.S. Cl.
USPC ............... 424/94.1; 424/94.2; 424/94.21

(58) Field of Classification Search
None
See application file for complete search history.

(56) References Cited

U.S. PATENT DOCUMENTS 4,943,530 A  7/1990  Christner et al.
7,153,503 B1  12/2006  Henderson

OTHER PUBLICATIONS

Barron J., *Lessons From the Miracle Doctors.* Healing America, Inc., May 1999.

Bracale G, Selvetella L., "Clinical study of the efficacy of and tolerance to seaprose S in inflammatory venous disease." *Minerva Cardioangiol* 44(10):515-524 (1996).
Braga PC, Moretti M et al., "Effects of seaprose on the rheology of bronchial mucus in patients with chronic bronchitis." *Int J Clin Pharmacol Res* 13(3):179-185 (1993).
Buck JE, Phillips N., "Trial of Chymoral in professional footballers." *Br J Clin Pract.* 24(9):375-7 (Sep. 1970).
Craig RP., "The quantitative evaluation of the use of oral proteolytic enzymes in the treatment of sprained ankles." *Injury.* 6(4):313-6 (May 1975).
Duskova M, Wald M., "Orally administered proteases in aesthetic surgery." *Aesthetic Plat Surg.* 23(1):41-4 (Jan.-Feb. 1999).
Fisher JD, Weeks RL, Curry WM, Hrinda ME, Rosen LL., "Effects of an oral enzyme preparation, Chymoral, upon serum proteins associated with injury (acute phase reactants) in man." *J Med.* 5(5):258-73 (1974).
Hoernecke R, Doenicke A., "Perioperative enzyme therapy. A significant supplement to postoperative pain therapy?"*Anaesthesist.* 42(12):856-61 (Dec. 1993).
Lie KK, Larsen RD, Posch JL., "Therapeutic value of oral proteolytic enzymes following hand surgery." *Arch Surg.* 98(1):103-4 (Jan. 1969).
Miller., "Proteolytic enzymes in inflammation: rationale for use." *Postgrad Med.* 19(1):16-22 (Jan. 1956).
Sumi H et al., "Enhancement of the fibrinolytic activity in plasma by oral administration of Nattokinase." *Acta Haematol* 84:139-143 (1990).
International Search Report and Written Opinion of PCT Application No. PCT/US07/075630, 2007.

*Primary Examiner* — Debbie K Ware
(74) *Attorney, Agent, or Firm* — Knobbe Martens Olson & Bear, LLP

(57) ABSTRACT

Preferred embodiments of the present invention relate to proteolytic enzyme formulations. More specifically, several embodiments relate to a proteolytic formulation to facilitate digestion, metabolism, degradation of target compounds, and systemic enzymatic action. Embodiments for improving oxygenation and reducing plaque are also provided.

7 Claims, No Drawings

PROTEOLYTIC ENZYME FORMULATIONS

RELATED APPLICATION

This application is a continuation of U.S. application Ser. No. 12/376,964, filed Sep. 15, 2009, now U.S. Pat. No. 8,287,858, which is the U.S. National Phase under 35 U.S.C. §371 of International Application No. PCT/US2007/075630, filed Aug. 9, 2007 (published as WO2008/021987A1), which claims the benefit of U.S. Provisional Application No. 60/836,824; filed Aug. 10, 2006, which applications are hereby incorporated by reference in their entirety for all purposes.

FIELD OF THE INVENTION

Preferred embodiments of the present invention relate to proteolytic enzyme formulations. More specifically, several embodiments relate to a proteolytic formulation comprising fungal protease, papain, bromelain, fungal pancreatin, nattokinase, protease-S, amylase, lipase, rutin, ginger, and CMIK-pH, to facilitate digestion, metabolism, degradation of target compounds, and systemic enzymatic action.

BACKGROUND OF THE INVENTION

Digestive enzymatic formulations are known in the art. In the book, *Lessons from the Miracle Doctors* (Baseline of Health, April 2002), Applicant describes the benefits of using proteolytic enzymes.

Prior to the formulations described herein, Applicant invented a proteolytic formulation with the following ingredients: fungal protease, papain, bromelain, fungal pancreatin, nattokinase, Seaprose-S, amylase, lipase, rutin, ginger, ionic minerals and vegetable stearate.

Preferred embodiments of the formulations described herein eliminate some of the above-identified ingredients and include new ingredients for optimal health benefits.

SUMMARY OF THE INVENTION

In one embodiment, a proteolytic formulation comprising fungal protease, papain, bromelain, fungal pancreatin, nattokinase, protease-S, amylase, lipase, rutin, ginger, and CMIK-pH is provided. The use of protease-S (also called endonase) in some preferred embodiments allows for greater stability and ease of manufacture, as compared to formulations having Seaprose-S. The use of CMIK-pH in some preferred embodiments not only improves the effectiveness of the proteolytic enzymes in the formulations, but also raises the blood pH levels in the entire body, which produces its own health benefits.

In one embodiment, the formulation is provided as a nutritional supplement. In another embodiment, the formulation is provided as an additive.

In one embodiment, the invention comprises a formulation comprising at least about: 300,000 HUT fungal protease, 72 MCU papain, 270 GDU bromelain, 1200 USP fungal pancreatin, 501 FU nattokinase, 15,000 U protease-S, 3,000 SKB amylase, 192 FIP lipase, 90 mg rutin, 30 mg ginger, and 240 mg CMIK-pH. In one embodiment, these dosages are provided in capsule form. In one embodiment, the formulation is adapted for oral administration.

In one embodiment, the invention comprises using the formulations described herein to prepare a medicament for preventing or reducing clot formation. In another embodiment, the invention comprises using the formulations described herein to prepare a medicament for preventing or reducing the release or migration of emboli. In yet another embodiment, the invention comprises using the formulations described herein to prepare a medicament for preventing or treating deep vein thrombosis.

In a further embodiment, the invention comprises using the formulations described herein to prepare a medicament for reducing scar tissue. In one embodiment, the invention comprises a method for preventing or treating sclerosis.

In an alternate embodiment, the invention comprises using the formulations described herein to prepare a medicament for facilitating digestion.

In still another embodiment, the invention comprises using the formulations described herein to prepare a medicament for reducing the concentration of impurities from the circulatory system or respiratory system.

In other embodiments, the invention comprises using the formulations described herein to prepare a medicament for preventing or reducing dental plaque. The formulation can be provided as a toothpaste or mouthwash. Dental floss comprising the formulation (e.g., as a coating or other component of the floss) may also be provided. Dental rinses in a dental office or formulations for home use are within the scope of several embodiments described herein. In some embodiments, a formulation is used to reduce plaque that has already formed. In other embodiments, an individual is instructed to use the formulation to prevent or reduce the formation of plaque.

In some embodiments, the invention comprises a method for raising the pH level of blood comprising administering an effective dose of the formulation to an individual. In some embodiments, the invention comprises using the formulation described above to prepare a medicament that raises the pH level of blood throughout the entire body. Raising the pH level of blood alleviates allergies and auto-immune diseases caused by circulating immune complexes (CICs), improves proteolytic enzyme reactions throughout the body, and increases the oxygen level in the blood.

DETAILED DESCRIPTION OF THE PREFERRED EMBODIMENTS

Preferred embodiments of the present invention relate to a nutraceutical formulation comprising one or more of the following compounds: fungal protease, papain, bromelain, fungal pancreatin, nattokinase, protease-S, amylase, lipase, rutin, ginger, and CMIK-pH. In one embodiment, all of the aforementioned compounds is provided.

In one embodiment, the invention comprises a systemic enzymatic formulation that is buffered. In one embodiment, CMIK-pH is used as the buffering agent. In another embodiment, other buffering agents are used in addition to, or instead of, CMIK-pH.

In one embodiment, a buffered formulation comprising fungal protease, papain, bromelain, fungal pancreatin, nattokinase, protease-S, amylase, lipase, rutin, ginger, and CMIK-pH has several advantages. First, the formulation optimizes the pH environment in the stomach and small intestine, which significantly enhances the enzymatic activity of the entire formulation. Second, the formulation will raise the body's pH, which will noticeably enhance the efficacy of the enzymes in every part of the body.

Thus, in one embodiment, a formulation comprising at least one of: fungal protease, papain, bromelain, fungal pancreatin, nattokinase, protease-S, amylase, lipase, rutin, and ginger is used in combination with a compound that increases the pH of the intestinal tract (such as CMIK-pH). The term "combination" as used herein, shall be given its ordinary meaning, and shall include solutions, suspensions, colloids, emulsions, dispersions, gels or mixtures.

Ingredients which may be used in several preferred embodiments of the invention are described below.

Fungal Protease

In one embodiment, a formulation comprising fungal protease is provided. In one embodiment, the formulation comprises fungal protease as the primary proteolytic enzyme and additionally includes one or more of the following compounds: papain, bromelain, fungal pancreatin, nattokinase, protease-S, amylase, lipase, rutin, ginger, and a buffering agent (such as CMIK-pH).

Animal-based proteases are typically destroyed in the stomach. By contrast, fungal (vegetarian-based) proteases are merely rendered inactive by stomach acid, not destroyed. As soon as a fungal protease passes into the alkaline environment of the intestinal tract, it reactivates, and, if not needed for digesting food, makes its way into the bloodstream.

Although fungal proteases reactivate in the intestinal tract, in some embodiments, formulations with a variety of digestive enzymes are provided. For example, in one embodiment, a formulation that includes enzymes that work optimally in a variety of pH ranges is provided. In other embodiments, enzymes that work in specific pH ranges are provided. CMIK-pH is particularly useful in those latter embodiments.

In several embodiments, a formulation comprising about 100,000 HUT to about 500,000 HUT of fungal protease is provided. In one embodiment, a formulation comprising about 300,000 HUT is provided. In some embodiments, formulations comprising less than 100,000 HUT or more than 500,000 HUT are provided. In some preferred embodiments, a vegetarian sourced fungal protease is provided.

In one embodiment, a formulation comprising fungal protease is used to break down and destroy unwanted fungi, bacteria, and/or viruses in the bloodstream.

Papain

In one embodiment, a formulation comprising papain is provided. Papain is one of the most widely used proteolytic enzymes, belonging to the thiol protease group. Thus, in one embodiment, a formulation comprising papain or another thiol protease is provided, in combination with one or more of the following compounds: fungal protease, bromelain, fungal pancreatin, nattokinase, protease-S, amylase, lipase, rutin, ginger, and a buffering agent (such as CMIK-pH).

In one embodiment, papain is derived the papaya fruit, such as from the juice of the unripe fruit, and is provided to facilitate digestion in an acid, alkaline, or neutral media. Thus, in some embodiments, papain is particularly beneficial because changes in intestinal alkalinity or acidity do not substantially interfere with the unique digestive activity of papain. Accordingly in some embodiments, a formulation comprising a digestive enzyme that functions in acidic, alkaline, or neutral media is provided.

In several embodiments, a formulation comprising about 25 MCU to about 150 MCU of papain is provided. In one embodiment, a formulation comprising about 72 MCU of papain is provided. In some embodiments, formulations comprising less than 25 MCU or more than 150 MCU are provided.

Bromelain

In one embodiment, a formulation comprising bromelain is provided. In one embodiment, a formulation comprising bromelain is provided in combination with one or more of the following compounds: fungal protease, papain, fungal pancreatin, nattokinase, protease-S, amylase, lipase, rutin, ginger, and a buffering agent (such as CMIK-pH).

Bromelain is a proteolytic digestive enzyme derived from pineapple stems that can enhance absorption of protein. Bromelain may also be derived from the ripe pineapple, unripe pineapple, and pineapple leaves.

In one embodiment, a formulation comprising bromelain is used to facilitate digestion. In another embodiment, a formulation comprising bromelain is used to increase protein turnover in the body including proteins found in joint tissue. In some embodiments, the broad substrate specificity of bromelain is used to efficiently hydrolyze most soluble proteins.

In one embodiment, a formulation comprising bromelain is provided as an anti-inflammatory enzyme useful in, for example, posttraumatic responses and swelling and after surgery. See Duskova M, Wald M. Orally administered proteases in aesthetic surgery. Aesthetic Plat Surg. 1999 January-February; 23(1):41-4; Hoemecke R, Doenicke A. Perioperative enzyme therapy. A significant supplement to postoperative pain therapy? Anaesthesist. 1993 December; 42(12):856-61; Lie K K, Larsen R D, Posch J L. Therapeutic value of oral proteolytic enzymes following hand surgery. Arch Surg. 1969 January; 98(1):103-4, all herein incorporated by reference. In some embodiments, a formulation comprising bromelain is used as part of an antiaging program to reduce tissue irritation.

In further embodiments, a formulation comprising bromelain is used to reduce platelet aggregation, arterial plaqueing, and clot formation. In one embodiment, a formulation comprising is provided to reduce joint inflammation in rheumatoid arthritis.

In several embodiments, a formulation comprising about 50 GDU to about 500 GDU of bromelain is provided. In one embodiment, a formulation comprising about 270 GDU of bromelain is provided. In some embodiments, formulations comprising less than 50 GDU or more than 500 GDU are provided.

Fungal Pancreatin

In one embodiment, a formulation comprising fungal pancreatin is provided. In one embodiment, a formulation comprising fungal pancreatin is provided in combination with one or more of the following compounds: fungal protease, papain, bromelain, nattokinase, protease-S, amylase, lipase, rutin, ginger, and a buffering agent (such as CMIK-pH).

Pancreatin is traditionally an animal derived enzyme that works in the small intestine. Thus, animal-based pancreatin typically works at a pH of about 6-8. Orally delivered pancreatin must be enterically coated so that the pancreatin can pass through the acidic stomach without being rendered ineffective. Because enteric coatings may dissolve incompletely, enteric coatings may reduce the overall activity of the enzyme. Plant based fungal pancreatin is able to function in a wider pH range.

Thus, in one embodiment, a formulation comprising plant based fungal pancreatin that is optimized for different pH levels is provided. In one embodiment, a formulation comprising fungal pancreatin is used to optimize the proteolytic process in all environments. In some embodiments, a formulation that accommodates pH levels changes through the digestive tract is provided. By using strains optimized for different pH's, formulations according to several embodiments of the invention assure that the proteolytic process is optimized in all environments.

In several embodiments, a formulation comprising about 400 USP to about 2000 USP of fungal pancreatin is provided. In one embodiment, a formulation comprising about 1200 USP of fungal pancreatin is provided. In some embodiments, formulations comprising less than 400 USP or more than 2000 USP are provided. In some preferred embodiments, vegetarian sourced fungal pancreatin is provided.

Nattokinase

In one embodiment, a formulation comprising nattokinase is provided. In one embodiment, a formulation comprising nattokinase is provided in combination with one or more of the following compounds: fungal protease, papain, bromelain, fungal pancreatin, protease-S, amylase, lipase, rutin, ginger, and a buffering agent (such as CMIK-pH).

Nattokinase is a potent fibrinolytic enzyme. In preferred embodiments, nattokinase is extracted and highly purified from a traditional soy-based Japanese food called Natto. Natto is a fermented cheese-like food that has been used in Japan for over 1000 years for its popular taste and as a folk remedy for heart and vascular diseases. While other soy foods contain enzymes, it is believed that only the natto preparation contains the specific nattokinase enzyme.

In one embodiment, a formulation comprising nattokinase is used to enhance the body's natural ability to fight blood clots. In some embodiments, a formulation comprising nattokinase is used to dissolve fibrin directly because it so closely resembles plasmin. See Sumi H et al. Enhancement of the fibrinolytic activity in plasma by oral administration of Nattokinase. Acta Haematol 1990; 84:139-143, herein incorporated by reference. In addition, a formulation comprising nattokinase is used to enhance the body's production of both plasmin and other clot-dissolving agents, including endogenous urokinase.

In several embodiments, a formulation comprising about 100 FU to about 1000 FU of nattokinase is provided. In one embodiment, a formulation comprising about 501 FU of nattokinase is provided. In some embodiments, formulations comprising less than 501 FU or more than 1000 FU are provided.

Protease-S

In one embodiment, a formulation comprising protease-S (also called endonase) is provided. Protease-S, in one preferred embodiment, is an enzyme preparation produced by apspergillus fermentation with broad specificity toward native and denatured proteins. In one embodiment, a formulation comprising protease-S is provided in combination with one or more of the following compounds: fungal protease, papain, bromelain, fungal pancreatin, nattokinase, amylase, lipase, rutin, ginger, and a buffering agent (such as CMIK-pH).

Protease-S is a newly discovered relative of the enzyme Seaprose-S. Protease-S has the benefits of Seaprose-S, but, in several preferred embodiments, surprisingly offers even better stability and allows for much easier handling during manufacturing. This characteristic allows for better tuning of the enzyme level in the formula. Moreover, the use of protease-S in some preferred embodiments permits a longer shelf life of the formulation. Accordingly, in preferred embodiments, the formulation does not contain Seaprose-S, and contains protease-S. However, in one embodiment, Seaprose-S may be used instead of, or in addition to, protease-S.

Seaprose-S and serrapeptase are commercially available enzymes with similar functions. However, Seaprose-S is more effective and better tolerated than serrapeptase. Moreover, the efficacy of Seaprose-S is assessed as good or excellent in 85% of test cases, as compared with 65% for serrapeptase. Seaprose-S also produces no adverse reactions, whereas serrapeptase may cause stomach upset. Seaprose-S is unaffected by stomach acid, whereas serrapeptase must typically be enterically coated to protect it from being destroyed by stomach acid. Thus, formulations comprising Seaprose-S instead of serrapeptase offer several advantages. However, as discussed earlier, substituting Seaprose-S with protease-S offers all of the above-identified advantages and provides unexpected additional advantages, including but not limited to, greater efficacy, little or no adverse effects, and acid stability. In addition, embodiments that comprise protease-S instead of Seaprose-S offer enhanced stability, and thus improved efficacy.

In several embodiments, formulations comprising protease-S provide one or more of the following benefits:
- anti-inflammatory effects;
- reduces pain and swelling in the body;
- cleans up arterial plaque;
- digests dead tissue, blood clots, and scar tissue;
- dissolves fibroid cysts;
- loosens and expels mucous; and
- helps relieve chronic sinusitis See Braga P C, Moretti M et al. Effects of seaprose on the rheology of bronchial mucus in patients with chronic bronchitis. Int J Clin Pharmacol Res 1993; 13(3):179-185; Bracale G, Selvetella L. Clinical study of the efficacy of and tolerance to seaprose S in inflammatory venous disease. Minerva Cardioangiol 1996; 44(10):515-524, all herein incorporated by reference.

In several embodiments, a formulation comprising about 5,000 U to about 25,000 U of protease-S is provided. In one embodiment, a formulation comprising about 15,000 U of protease-S is provided. In some embodiments, formulations comprising less than 5,000 U or more than 25,000 U are provided.

Amylase

In one embodiment, a formulation comprising amylase is provided. In one embodiment, a formulation comprising amylase is provided in combination with one or more of the following compounds: fungal protease, papain, bromelain, fungal pancreatin, nattokinase, protease-S, lipase, rutin, ginger, and a buffering agent (such as CMIK-pH).

Amylase is an enzyme that facilitates the break down and assimilation of starches and carbohydrates. Supplemental amylase can also help reduce stress. Amylases are derived from animal and vegetarian (fungal and plant) sources.

In several embodiments, a formulation comprising about 1,000 SKB to about 5,000 SKB of amylase is provided. In one embodiment, a formulation comprising about 3,000 SKB of amylase is provided. In some embodiments, formulations comprising less than 1,000 SKB or more than 5,000 SKB are provided. In preferred embodiments, vegetarian sourced amylase is provided.

Lipase

In one embodiment, a formulation comprising lipase is provided. In one embodiment, a formulation comprising lipase is provided in combination with one or more of the following compounds: fungal protease, papain, bromelain, fungal pancreatin, nattokinase, protease-S, amylase, rutin, ginger, and a buffering agent (such as CMIK-pH).

Lipase contributes to carbohydrate and fat digestive action. When added to a meal as a supplement, lipase digests dietary fat, relieving the gallbladder, liver and the pancreas, which would otherwise need to produce the required enzymes. Protein absorption from fatty foods such as fish or seeds can be improved by incorporating supplemental lipase enzymes in the diet.

In several embodiments, a formulation comprising about 50 FIP to about 500 FIP of lipase is provided. In one embodiment, a formulation comprising about 192 FIP of lipase is provided. In some embodiments, formulations comprising less than 50 FIP or more than 500 FIP are provided. In preferred embodiments, vegetarian sourced lipase is provided.

Rutin

In one embodiment, a formulation comprising rutin is provided. In one embodiment, a formulation comprising rutin is provided in combination with one or more of the following compounds: fungal protease, papain, bromelain, fungal pancreatin, nattokinase, protease-S, amylase, lipase, ginger, and a buffering agent (such as CMIK-pH).

Rutin is a flavonol, a subclass of the bioflavonoids. In one embodiment, a formulation comprising rutin is used to strengthen capillaries, and is particularly useful for those who bruise or bleed easily.

In several embodiments, a formulation comprising about 30 mg to about 200 mg of rutin is provided. In one embodiment, a formulation comprising about 90 mg of rutin is provided. In some embodiments, formulations comprising less than 30 mg or more than 200 mg are provided.

Ginger

In one embodiment, a formulation comprising ginger is provided. In one embodiment, a formulation comprising ginger is provided in combination with one or more of the following compounds: fungal protease, papain, bromelain, fungal pancreatin, nattokinase, protease-S, amylase, lipase, rutin, and a buffering agent (such as CMIK-pH).

Ginger has a long history of use in herbal medicine. In some embodiments, a formulation comprising ginger is used for its strong anti-viral properties. In several embodiments, a formulation comprising ginger is used to control nausea, which makes it useful in treating motion sickness, chemotherapy, radiation, morning sickness during pregnancy, as well as in intestinal activating and detoxing formulas, and in liver cleansing programs.

In several embodiments, a formulation comprising ginger is used as a COX 2 inhibitor, thus relieving inflammation and pain in the body. In some embodiments, a formulation comprising ginger is used for common inflammation observed in a knee or shoulder, as well inflammation throughout the body. In one embodiment, a formulation comprising ginger is used to reduce neuronal inflammation, and may be used in cerebral degenerative diseases, such as Alzheimer's.

Because COX 2 may play a major role in the onset of many forms of cancer (including colon, skin, bladder, esophagus, and pancreas), arthritis, and Alzheimer's Disease, a formulation comprising ginger is used to ameliorate these conditions.

In several embodiments, a formulation comprising about 10 mg to about 100 mg of ginger is provided. In one embodiment, a formulation comprising about 30 mg of ginger is provided. In some embodiments, formulations comprising less than 10 mg or more than 100 mg are provided.

CMIK-pH

In one embodiment, a formulation comprising one or more buffering agents, such as CMIK-pH, is provided. In one embodiment, a formulation comprising CMIK-pH is provided in combination with one or more of the following compounds: fungal protease, papain, bromelain, fungal pancreatin, nattokinase, protease-S, amylase, lipase, rutin, and ginger.

CMIK-pH is a buffering agent. CMIK-pH comprises calcium, magnesium, ionic trace minerals, and potassium. In one embodiment, a formulation comprising CMIK-pH optimizes the pH environment in the stomach and small intestine, which will significantly enhance the enzymatic activity of the entire formula. Enzymes included in certain embodiments of the present invention work best at a specific pH and become inactive outside of a narrow range. Proteolytic enzymes, other than pepsin, work best in a neutral slightly alkaline environment. The use of CMIK-pH ensures that the proteolytic enzymes in the formula remain at their optimal pH level. The greater effectiveness resulting from having the proper pH balance allows the use of a lower enzyme dosage for the same level of efficacy. In another embodiment, CMIK-pH provides extra protection for the proteolytic enzymes from stomach acid.

In several embodiments, a formulation comprising CMIK-pH raises the blood's pH throughout the body, which will noticeably enhance the efficacy of proteolytic enzymes in every part of the body, including pre-existing proteolytic enzymes not ingested as part of the formulation. In one embodiment, CMIK-pH effectively optimizes the pH of soft tissue in the body by eliminating the body's need to raise blood pH by borrowing minerals from soft tissue. This improves the ability of proteolytic enzymes to root out CICs embedded in that soft tissue, thus relieving allergies and reducing the possibility of autoimmune conditions.

In several embodiments, CMIK-pH is used instead of ionic minerals alone. Ionic minerals may be used as coenzyme factors that increase the efficacy of enzymes in several embodiments. However, CMIK-pH is used in some preferred embodiments because calcium, magnesium, and especially potassium are pH buffering minerals that optimize alkalinity. A proper alkaline environment in a person's blood provides thousands of times the oxygen needed for all bodily functions. Having the proper pH balance in the body is a major factor in optimizing health and preventing disease.

In one embodiment, CMIK-pH helps optimize the pH of soft tissue. The human body is adapted to "steal" minerals and lower pH in soft tissue to protect the blood if an individual's diet is too acidic. The typical Western diet consists of highly acid-forming foods, including meats, dairy, cooked grains, desserts, and certain fruit. The CMIK-pH, according to several formulations described herein, raise soft tissue pH and improve the ability of proteolytic enzymes to remove any CICs embedded in that soft tissue, thus relieving allergies and reducing the possibility of autoimmune conditions.

In another embodiment, CMIK-pH prevents or treats osteoporosis by providing a source of buffering minerals. The presence of CMIK-pH reduces depletion of important minerals in the bone, thereby increase bone mineral density and preventing or treating osteoporosis.

Because, in some embodiments, CMIK-pH will provide the body with an easily accessible source of buffering minerals, the body will not have to resort from commandeering such minerals from soft tissue, bone, or other places where minerals are needed.

In several embodiments, a formulation comprising about 50 mg to about 500 mg of CMIK-pH is provided. In one embodiment, a formulation comprising about 240 mg of CMIK-pH is provided. In some embodiments, formulations comprising less than 50 mg or more than 500 mg are provided. In one embodiment, CMIK-pH comprises equal amounts of calcium, magnesium, ionic trace minerals, and potassium. In other embodiments, CMIK-pH comprises 10-50% calcium, 10-50% magnesium, 10-50% magnesium, and less than 10% ionic trace minerals.

The use of powders and/or extracts of the components of the formulations provided herein is within the scope of preferred embodiments of the present invention.

Formulations

In several embodiments, the invention comprises a formulation comprising: 300,000 HUT fungal protease, 72 MCU papain, 270 GDU bromelain, 1200 USP fungal pancreatin, 501 FU nattokinase, 15,000 U protease-S, 3,000 SKB amylase, 192 FIP lipase, 90 mg rutin, 30 mg ginger, and 240 mg CMIK-pH. In one embodiment, these dosages are provided in capsule form. In one embodiment, a single capsule contains the ingredients in the stated amounts.

In one embodiment, a formulation is provided for detoxifying the body. In one embodiment, a user is directed to start with 2 capsules three times a day and build to 4 capsules or more until noticeable benefits are observed. In one embodiment, a detoxification program lasts about 30 days to about 2 years.

In one embodiment, a formulation is provided for maintaining good health. In one embodiment, a user is directed to take from 3-10 capsules a day (depending on desired outcome) at least 1 hour before or after eating.

The ingredients used for preferred embodiments described herein may be obtained commercially.

In some embodiments, formulations comprising fungal protease, papain, bromelain, fungal pancreatin, nattokinase, protease-S, amylase, lipase, rutin, ginger, and CMIK-pH additionally comprise one or more of the following agents or compounds: vitamins, minerals, antioxidants, and other enzymes or catalysts.

In several preferred embodiments, the formulations described herein are prepared for use as a supplement. The formulations may be provided as tinctures, capsules and tablets for oral use.

In one embodiment, formulations may be provided as an additive to foods. Food products to which the compositions described above may be added include, but are not limited to beverages, baked goods, soups, cereals and packaged foods. Energy bars or nutritional bars may be particularly suitable for the addition of the formulations described herein. Suitable beverages include soft drinks such as coffee, tea, herbal tea, milk, fruit juice, water, carbonated beverages (e.g., soda, water, juice), soy milk and rice milk.

In one embodiment, the invention a formulation of proteolytic enzymes is provided to ease the burden on the body, so it no longer has to divert its resources.

In another embodiment, the invention comprises a method of augmenting the proteolytic functions of metabolic enzymes. In one embodiment, a formulation according to any one of the embodiments described herein is administered to an individual. After administration, one or more of proteolytic enzymes present in the formulation enter the bloodstream and facilitate endogenous metabolic processes (by, e.g., augmenting endogenous enzymes, acting as catalysts, etc).

In one embodiment, the invention comprises a method for reducing inflammation. Inflammation is a natural response of the body to injury. However, excessive inflammation retards the healing process. Several embodiments of the formulations described herein may reduce inflammation by neutralizing the biochemicals of inflammation (e.g., bradykinins and pro-inflammatory eicosanoids) to levels at which the synthesis, repair and regeneration of injured tissues can take place. See Miller. Proteolytic enzymes in inflammation: rationale for use. Postgrad Med. 1956 January; 19(1):16-22, herein incorporated by reference. Reducing inflammation can have immediate impact on improved heart health, cancer prevention and recovery, and Alzheimer's prevention. Reducing inflammation also helps speed up recovery from sprains, strains, fractures, bruises, contusions, surgery and arthritis. See Buck J E, Phillips N. Trial of Chymoral in professional footballers. Br J Clin Pract. 1970 September; 24(9):375-7; Craig R P. The quantitative evaluation of the use of oral proteolytic enzymes in the treatment of sprained ankles. Injury. 1975 May; 6(4):313-6; Fisher J D, Weeks R L, Curry W M, Hrinda M E, Rosen L L. Effects of an oral enzyme preparation, Chymoral, upon serum proteins associated with injury (acute phase reactants) in man. J Med. 1974; 5(5):258-73, all herein incorporated by reference.

In another embodiment, the invention comprises a method for cleansing the blood of debris. Several embodiments of the formulations described herein may metabolize or degrade organic debris in the circulatory and lymph systems.

In yet another embodiment, the invention comprises a method for reducing blood clots. Several embodiments of the formulations described herein may reduce blood clots by dissolving or otherwise degrading fibrin in the blood. Thus, in some embodiments, the invention comprises the use of any one of the formulations described herein for the treatment or prevention of stroke. In other embodiments, the invention comprises the use of any one of the formulations described herein for the treatment or prevention of DVT (deep vein thrombosis).

DVT primarily affects the veins in the lower leg and the thigh. Typically, a clot or thrombus forms in the larger veins and interfere with circulation. The clot may embolize and lodge in the lungs, brain, heart, or other area, and cause major damage to the area. The risk of DVT increases with prolonged immobilization. Accordingly, in one embodiment, the invention comprises a method of preventing or treating DVT. By administering a formulation according to any of the embodiments described herein, the formation and/or release of clots may be reduced, thereby reducing the risk of DVT. In some embodiments, the invention comprises a method of marketing a formulation according to any of the embodiments described herein to airline passengers as a means to reduce the risk of developing DVT on flights. In other embodiments, the invention comprises a method of marketing a formulation according to any of the embodiments to any group of individuals that will be immobilized for long periods of time (e.g., greater than about 1 hour), such as bed-rest patients, and individuals traveling on long car, boat or train trips.

In a further embodiment, the invention comprises a method for enhancing the immune system. By administering a formulation according to any of the embodiments described herein, the activity of macrophages and other immune cells are supplemented.

In one embodiment, the invention comprises a method for reducing the concentration of undesired bacteria, viruses, molds and fungi. Bacteria, viruses, molds and fungi are protein/amino acid-based. By administering a formulation according to some of the embodiments described herein, bacteria, viruses, molds and fungi are digested in, for example, the bloodstream.

In another embodiment, the invention comprises a method for preventing or treating auto-immune disorders. Some auto-immune disorders are the result of large, undigested proteins that make their way into the bloodstream and form CICs. The CICs can trigger allergies and autoimmune diseases. By administering a formulation according to some of the embodiments described herein, CICs in the body are reduced, deactivated or eliminated, thereby ameliorating allergies and autoimmune conditions. In some embodiments, the formulation is particularly effective for sinusitis and asthma.

In a further embodiment, the invention is used in the treatment of multiple sclerosis. Multiple sclerosis is an autoimmune disease affecting the central nervous system. In multiple sclerosis, the myelin tissue that normally surrounds the nerve fibers is disrupted, leaving scar tissue (sclerosis) in its place. Some embodiments of the formulations described herein are useful for dissolving or degrading the sclerosis, thereby ameliorating the symptoms of multiple sclerosis.

In a further embodiment, the invention comprises a method for detoxifying the body by removing undesired compounds and impurities from the digestive, circulatory or respiratory system. In some embodiments, reducing the concentration of undesired agents from the respiratory system is particularly beneficial. In some embodiments, a formulation according to some of the embodiments described herein is used to reduce the amount of mucous in the lungs. In yet other embodiments, a formulation is provided to improve breathing for individuals with allergies, emphysema, and Chronic Obstructive Pulmonary Disease.

In another embodiment, the invention comprises a method for reducing scar tissue. Scar tissue is made of protein. By administering a formulation according to some of the embodiments described herein, scar tissue is effectively digested or dissolved. Some preferred embodiments are particularly effective at reducing internal scar tissue in, for example, the circulatory system. In one embodiment, a formulation according to some of the embodiments described herein is used to specifically reduce arterial scar tissue. In some embodiment, scar tissue is effectively degraded, while leaving healthy tissue in tact.

In yet another embodiment, the invention comprises a method for reducing inflammation by administering effective doses of a formulation according to some of the embodiments described herein. In one embodiment, arterial inflammation is reduced. In another embodiment, a general reduction of inflammation reduces pain levels. A reduction in inflammation may also slow the aging process at a cellular level. A reduction in inflammation may also ameliorate dermatological conditions that are caused by inflammation of the dermis, epidermis, or surrounding tissue.

In yet another embodiment, the invention comprises a method for reducing acid reflux or gastroesophageal reflux disease (GERD).

In a further embodiment, the invention comprises a method for increasing oxygen flow, in for example, blood or other tissue. In one embodiment, the invention comprises a method for increasing recovery (thereby decreasing time for recovery) by improving oxygen flow in the blood. Formulations of several embodiments of the invention may also be administered to increase muscle development by improving oxygen flow in the blood, and may be particularly beneficial to those individuals engaged in muscle building activities, such as body building.

In one embodiment, the present invention comprises a formulation for dental applications. In one embodiment, the invention comprises a method of dissolving, degrading, and/or reducing dental plaque. By administering formulations according to some of the embodiments disclosed herein, the bacterial component of plaque is degraded, and the plaque can easily be rinsed away. Thus, in some embodiments, a formulation is provided as a toothpaste or mouthwash. In other embodiments, a formulation is provided as a coating for dental floss.

In another embodiment, the invention comprises a method for reducing arterial plaque. In one embodiment, a formulation is provided dissolve fibrin that holds the plaque together, thereby reducing the concentration of plaque in an artery or other vessel.

The compositions described herein can be used per se, or in compositions where they are mixed with other active ingredients, suitable carriers or excipient(s). The term composition, as used herein, can be used interchangeably with the term formulation. Techniques for formulation and administration of the compounds of the instant application may be found in "Remington's Pharmaceutical Sciences," Mack Publishing Co., Easton, Pa., 18th edition, 1990.

The formulations according to several embodiments described herein may be administered via several routes of administration. Suitable routes of administration include, but are not limited to, oral, buccal, sublingual, rectal, topical, transmucosal, or intestinal administration; parenteral delivery, including intramuscular, subcutaneous, intravenous, intramedullary injections, as well as intrathecal, direct intraventricular, intraperitoneal, intranasal, or intraocular injections.

Alternately, one may administer the compound in a local rather than systemic manner, for example, via injection of the compound directly in the renal or cardiac area, often in a depot or sustained release formulation. Further, one may administer the composition in a targeted delivery system, for example, in a liposome coated with a tissue-specific antibody. The liposomes will be targeted to and taken up selectively by the organ. Controlled release oral formulations are also provided in one embodiment.

The compositions of the several embodiments of the present invention may be manufactured in a manner that is itself known, e.g., by means of conventional mixing, dissolving, granulating, dragee-making, levigating, emulsifying, encapsulating, entrapping or tableting processes.

Compositions for use in accordance with preferred embodiments of the present invention thus may be formulated in conventional manner using one or more physiologically acceptable carriers comprising excipients and auxiliaries which facilitate processing of the active compounds into suitable preparations. Proper formulation is dependent upon the route of administration chosen. Any of the well-known techniques, carriers, and excipients may be used as suitable and as understood in the art; e.g., in Remington's Pharmaceutical Sciences, above.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with carriers well known in the art. Such carriers enable the compounds of the invention to be formulated as tablets, pills, dragees, capsules, liquids, gels, syrups, slurries, suspensions, tinctures and the like, for buccal administration, sublingual administration or oral ingestion. Preparations for oral use can be obtained by mixing with one or more solid excipients, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

For topical administration, the compounds may be formulated for administration to the epidermis as ointments, gels, creams, pastes, salves, gels, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Preparations which can be used orally, including sublingually, which include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Formulations for oral administration should be in dosages suitable for such administration.

For buccal administration, the compositions may take the form of tablets lozenges or tinctures formulated in conventional manner.

For administration by inhalation, the compounds for use according to several embodiments of the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Compositions suitable for use according to several embodiments of the present invention include compositions where the active ingredients are contained in an amount effective to achieve its intended purpose. More specifically, an effective amount means an amount of compound effective to enhance energy levels, stimulate pleasure centers in the brain and/or body, or to suppress the appetite. Determination of an effective amount is well within the capability of those skilled in the art, especially in light of the detailed disclosure provided herein.

In several embodiments described herein, methods of treating a certain condition, disorder, or disease described herein also include methods of preventing said condition, disorder, or disease. Thus, several embodiments of the invention comprise providing a formulation described herein and instructing a user to take the formulation as a preventive measure, or as a measure that will reduce the likelihood of developing said condition, disorder, or disease. In some embodiments, the dose for prevention will be the same as the dose for treatment. In other embodiments, the dose for prevention will be in the range of about 25%-75% of the dose for treatment.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A proteolytic formulation comprising:
fungal protease;
papain;
bromelain;
fungal pancreatin;
nattokinase;
Seaprose S in powder form;
amylase;
lipase;
rutin;
ginger; and
a combination of calcium, magnesium, ionic trace minerals, and potassium (CMIK-pH).

2. The proteolytic formulation of claim 1, wherein:
wherein said fungal protease is provided in a dose of about 100,000 HUT to about 500,000 HUT;
wherein said papain is provided in a dose of about 25 MCU to about 150 MCU;
wherein said bromelain is provided in a dose of about 50 GDU to about 500 GDU;
wherein said fungal pancreatin is provided in a dose of about 400 USP to about 2000 USP;
wherein said nattokinase is provided in a dose of about 100 FU to about 1000 FU;
wherein said amylase is provided in a dose of about 1,000 SKB to about 5,000 SKB;
wherein said lipase is provided in a dose of about 50 FIP to about 500 FIP;
wherein said rutin is provided in a dose of about 30 mg to about 200 mg;

wherein said ginger is provided in a dose of about 10 mg to about 100 mg; and wherein said CMIK-pH is provided in a dose of about 50 mg to about 500 mg.

3. The proteolytic formulation of claim 1, wherein said formulation is provided in a tablet or capsule form for oral administration.

4. The proteolytic formulation of claim 1, wherein said formulation is provided as a tincture for oral administration.

5. The proteolytic formulation of claim 1, wherein said formulation is configured for topical administration.

6. The proteolytic formulation of claim 1, wherein said formulation is provided as a toothpaste, a mouthwash, or a dental floss coating to facilitate dental plaque reduction.

7. A proteolytic formulation comprising Seaprose S in powder form and a combination of calcium, magnesium, ionic trace minerals, and potassium (CMIK-pH).

\* \* \* \* \*